:::cover
United States Patent [19]

Cardis

[11] Patent Number: 4,717,491

[45] Date of Patent: Jan. 5, 1988

[54] REACTION PRODUCTS OF DIALKYL AND TRIALKYL PHOSPHITES WITH ELEMENTAL SULFUR, ORGANIC COMPOSITIONS CONTAINING SAME, AND THEIR USE IN LUBRICANT COMPOSITIONS

[75] Inventor: Angeline B. Cardis, Florence, N.J.

[73] Assignee: Mobil Oil Corporation, New York, N.Y.

[21] Appl. No.: 883,665

[22] Filed: Jul. 9, 1986

[51] Int. Cl.$^4$ .......................................... C10M 135/02
[52] U.S. Cl. ...................................... 252/46.7; 568/14
[58] Field of Search .......................... 252/46.7; 568/14

[56] References Cited

U.S. PATENT DOCUMENTS 4,152,275  5/1979  Howdysky et al. ............... 252/46.6
4,207,195  6/1980  Howdysky ........................ 252/46.6

*Primary Examiner*—Jacqueline V. Howard
*Attorney, Agent, or Firm*—Alexander J. McKillop; Michael G. Gilman; Van D. Harrison, Jr.

[57] ABSTRACT

Dialkyl and trialkyl phosphites are reacted with sulfur. The resulting product is further reacted with an amine, olefin, or alkylene oxide to form a lube oil product. A better additive results when addition phosphorus trioxide is then reacted with the resulting product.

9 Claims, No Drawings
:::

REACTION PRODUCTS OF DIALKYL AND TRIALKYL PHOSPHITES WITH ELEMENTAL SULFUR, ORGANIC COMPOSITIONS CONTAINING SAME, AND THEIR USE IN LUBRICANT COMPOSITIONS

NATURE OF THE INVENTION

This invention relates to reaction products of dialkyl and trialkyl phosphites with elemental sulfur, reaction of the resulting product with epoxides, olefins, and amines, and use of these products in lubricating oil formulations.

PRIOR ART

U.S. Pat. No. 3,984,448 discloses the use of metal oxides, such as those of copper, calcium, barium, magnesium, zinc, cadmium, titanium or lead in conjunction with elemental sulfur and O,O-dialkylphosphorus acid esters to produce dialkyl thiophosphates.

U.S. Pat. No. 4,242,511 discloses the reaction of O,S-dialkylthiophosphoric acids esters by subjecting a thiophosphate to partial dealkylation in forming the salt of the dealkylated product by treatment with an amine.

Although dithiophosphate products are known lubricant additives, their preparation involves processes resulting in noxious, undesirable by-products such as hydrogen sulfide and chloride-containing waste streams. Accordingly a primary object of this invention is to provide a process for preparing thiophosphate products which eliminates the production of the aforementioned undesirable by-products.

SUMMARY OF THE INVENTION

In brief, this invention comprises in one aspect reacting dialkyl or trialkyl phosphites with elemental sulfur to provide an intermediate reactive product and then further reacting this intermediate product with epoxides, olefins, or amines to obtain a desired lube oil additive. In another aspect this invention comprises reacting the product thus obtained with phosphorus pentoxide to obtain a second improved lube oil additive. This invention also comprises a method for preparing lube oils wherein the aforedescribed additives are added to a selected lubricating oil. This invention further comprises the resulting lube oil product.

DESCRIPTION OF THE INVENTION

In the present invention an intermediate reaction product is obtained by reacting dialkyl or trialkyl phosphites of the general formula

$(R_1O)_2POR_2$ where $R_1$ is a hydrocarbon radical of 4 to 18 carbon atoms and $R_2$ is hydrogen or a hydrocarbon radical of 4 to 18 carbon atoms with elemental sulfur in the absence of any added catalyst in the presence of pulverulent sulfur at elevated temperature. Useful dialkyl or trialkyl phosphites include oleyl, phenyl, nonyl phenyl, octyl-phenyl, 2-ethyl hexyl, 1,3-dimethylbutyl, tridecyl, isodecyl, octyl and butyl, and mixed phosphites of the above radicals. If desirable, an unreactive organic solvent can be utilized. Preferably the organic solvent is selected from benzene, toluene, xylene, and mixed alkyl and aromatic petroleum distillates.

The pulverulent sulfur should conveniently have a mean particle size of less than one millimeter, preferably less than 0.01 millimeters, as this enables the reaction to be shortened. Reaction temperatures between 75° and 110° C. are preferred and a mole ratio of sulfur to phosphite of 0.8 to 1.2 is preferred. The reaction is carried out, preferably under a blanket of material such as nitrogen or other non-reactive gas. At the end of the reaction period the reaction mixture is allowed to cool to room temperature. The desired product is then stripped under vacuum to remove solvent and volatile byproducts and can be subsequently filtered or decanted from the reaction vessel.

This intermediate reaction product thus obtained is then further reacted with an amine, olefin, or alkaline oxide. The mole ratio of one of these reactants reacted with one mole of phosphite in the reaction product is 0.9 to 1.2. This second reaction is effected by mixing the reactants and allowing them to react (with added heat, if desirable) at a temperature between about 10° C. and about 90° C. The final product obtained can then be separated and purified by filtration and decantation. This product is then suitable for use in lube oil and grease formulations.

The amine compound to be reacted with the product formed by the alkyl phosphite and sulfur can be primary, secondary or tertiary. Preferred amines include Primene 81R, benzotriazole, tolutriazole, amine-containing polymeric succinimides, and aromatic amines such as dialkyl diphenylamine and (alkylated) phenyl naphthylamines.

If olefins are to be utilized they can be selected from vinyl ethers, esters and amides and other such activated olefins.

Useful alkylene oxides include ethylene oxide and propylene oxide.

As indicated previously, although the product obtained is useful as a lube oil additive it provides a product of improved performance if it is further reacted with phosphorus pentoxide, $P_2O_5$ in a mole ratio of about 1 mole of $P_2O_5$ to about 3 moles of thiophosphate product.

The resulting reaction products of this invention are used with lubricating oils or greases to the extent of from about 0.1% to about 10% by weight of the total composition. Furthermore, other additives, such as detergents, antioxidants, antiwear agents and the like may be present. These can include phenates, sulfonates, succinimides, zinc dialkyl dithiophosphates, polymers, calcium and magnesium salts of phenates and sulfonates, including overbased salts of the same, and the like.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexene, octene, decene, and dodecene, etc. These vicinal diols are especially effective in synthetic oils formulated using mixtures of synthetic hydrocarbon olefin oligomers and lesser amounts of hydrocarbyl carboxylate ester fluids. The other synthetic oils, which can be used alone with the compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

Having described the invention in general aspects, the following examples are offered as specific illustrations. Parts are by weight.

EXAMPLE 1

To 388 g (2.0 moles) dibutylhydrogen phosphite was added 64 g (2.0 moles) sulfur. The temperature was raised to 100° C. under a nitrogen atmosphere with stirring and held for eight hours.

The reaction mixture was cooled to ambient temperature and then held in an ice bath as propylene oxide (204 g, 3.5 moles) was added over one and one-half hours. The temperature was increased to reflux the excess propylene oxide (pot temperature=90° C.). After two hours, the excess propylene oxide had distilled up the condenser. Heptane (100 cc) was added, and refluxing was continued an additional three hours. The solvent was distilled off and the product was vacuum topped at 20 mm Hg, 100° C.

The product was cooled to 50° C. and filtered through diatomaceous earth.

EXAMPLE 2

The product of Example 1 (113.6 g, 0.2 moles) was stirred at 50° C. under nitrogen as phosphorus pentoxide (9.5 g, 0.066 moles) was added in portions over forty-five minutes. The temperature was raised to 75° C. and held two and one-half hours. The product was then filtered.

The recovered filtrate, the product, was stirred at 50° C. as Primene 81R (21.7 g) was added dropwise over twenty minutes. Primene 81R is a mixed $C_{12}$ to $C_{14}$ tertiary alkyl primary amine produced and sold commercially by Rohm and Haas Co. This final product was stirred an additional hour at 50° C.

Following the procedures of Examples 1 and 2, products were prepared from dilaurylhydrogen phosphite, bis-2-ethylhexylhydrogen phosphite, and dioleylhydrogen phosphite.

EXAMPLE 3

Sulfur (32 g, 1.0 mole) and bis-(2-ethylhexyl) hydrogen phosphite (306 g, 1.0 mole) were stirred under nitrogen as the temperature was increased from ambient to 100° C. At 100° C., Primene 81R (191 grams) was added dropwise over twenty minutes. After the addition, stirring was continued an additional hour at 100° C. The temperature was reduced to 50° C. and the product was filtered through diatomaceous earth.

Following the procedure of Example 3, products were also made from dibutylhydrogen phosphite, dioleylhydrogen phosphite, and dilaurylhydrogen phosphite.

EVALUATION OF PRODUCTS

The products described herein were blended in mineral oil and tested in the Shell Four-Ball Wear Test. The results in Table 1 demonstrate the antiwear protection afforded by these products. The mineral oil blends were further evaluated for EP properties in the Four-Ball Weld Test. The results are listed in Table 2.

TABLE 1

FOUR BALL WEAR TEST SCAR DIAMETER (MM)
¼ Inch Balls, 52100 Steel, 60 Kg., 30 Minutes, 1.5%

| Example | R | Temp., °F. | 1000 RPM | 2000 RPM |
|---|---|---|---|---|
| Base Stock | | 200 | 1.5 | 2.0 |
| | | 390 | 1.8 | 1.9 |
| 1 | Butyl | 200 | 0.53 | 0.8 |
| | | 390 | 0.8 | 0.75 |
| 1 | 2-Ethylhexyl | 200 | 0.55 | 0.5 |
| | | 390 | 1.6 | 1.6 |

TABLE 1-continued

FOUR BALL WEAR TEST SCAR DIAMETER (MM)
½ Inch Balls, 52100 Steel, 60 Kg., 30 Minutes, 1.5%

| Example | R | Temp., °F. | 1000 RPM | 2000 RPM |
|---|---|---|---|---|
| 1 | Lauryl | 200 | 0.55 | 0.5 |
|   |        | 390 | 1.4  | 1.9 |
| 1 | Oleyl  | 200 | 0.6  | 1.6 |
|   |        | 390 | 1.1  | 1.7 |
| 2 | Butyl  | 200 | 0.5  | 0.7 |
|   |        | 390 | 1.2  | 1.7 |
| 2 | 2-Ethylhexyl | 200 | | |
|   |        | 390 | | |
| 2 | Lauryl | 200 | | |
|   |        | 390 | | |
| 2 | Oleyl  | 200 | 0.5  | 0.8 |
|   |        | 390 | 1.7  | 1.8 |
| 3 | Butyl  | 200 | 0.5  | 0.5 |
|   |        | 390 | 1.1  | 1.8 |
| 3 | 2-Ethylhexyl | 200 | 0.55 | 0.75 |
|   |        | 390 | 0.55 | 1.75 |
| 3 | Lauryl | 200 | 0.5  | 1.5 |
|   |        | 390 | 0.8  | 1.7 |
| 3 | Oleyl  | 200 | 0.4  | 0.6 |
|   |        | 390 | 1.4  | 1.7 |

TABLE 2

FOUR-BALL WELD, 1.5% ADDITIVE CONCENTRATION

| Example | R | Weld Load (Kg) | Mean Hertz Load |
|---|---|---|---|
| Base Stock | | 126 | 26.9 |
| 1 | Butyl | 200 | 46.6 |
| 1 | 2-Ethylhexyl | 160 | 37.1 |
| 1 | Lauryl | 160 | 34.4 |
| 1 | Oleyl | 160 | 41.1 |
| 2 | Butyl | 200 | 40.9 |
| 2 | 2-Ethylhexyl | | |
| 2 | Lauryl | | |
| 2 | Oleyl | 200 | 40.6 |
| 3 | Butyl | 200 | 46.3 |
| 3 | 2-Ethylhexyl | 200 | 43.6 |
| 3 | Lauryl | 200 | 48.4 |
| 3 | Oleyl | 200 | 41.2 |

What is claimed is:

1. A process for making a reaction product suitable for use as an additive in lubricating oils comprising
   (a) reacting a dialkyl or trialkyl phosphite with elemental sulfur in a mole ratio of sulfur to phosphite of between about 0.8 and about 1.2 at a temperature between about 75° and about 110° C. and in the absence of any catalytic material added to promote reaction of the two reactants:
   (b) separating the reaction product thereby obtained;
   (c) reacting the reaction product from (b) with an amine in a mole ratio of amine to phosphite of about 0.9 to about 1.2, at a temperature between about 10° and about 90° C.: and
   (d) separating from the resulting reaction mixture the desired product.

2. The process of claim 1 wherein said phosphite has the structural formula $(R_1O)_2POR_2$ where $R_1$ is an alkyl hydrocarbon radical of 4 to 18 carbon atoms and $R_2$ is hydrogen or the same or a different alkyl hydrocarbon radical of 4 to 18 carbon atoms.

3. The process of claim 1 wherein the dialkyl or trialkyl phosphite is selected from the group consisting of oleyl, phenyl, nonylphenyl, octylphenyl, 2-ethyl hexyl, 1,3-dimethyl butyl, tridecyl, isodecyl, octyl, butyl, and mixed phosphites.

4. The reaction product produced by the process of claim 1.

5. The reaction product of claim 4 wherein the amine is selected from the group consisting of mixed $C_{12}$ to $C_{14}$ tertiary alkyl primary amines, benzotriazole and tolutriazole.

6. The reaction product of claim 4, wherein the amine is selected from the group consisting of amine-containing polymeric succinimide, and aromatic amines.

7. A lubricant compositon comprising a lubricant and between about 0.1% and about 10% by weight of the total composition of the reaction product resulting from the process of claim 1.

8. A lubricant composition comprising a lubricant and between about 0.1% and about 10% by weight of the total composition of the reaction product resulting from the process of claim 2.

9. A lubricant composition comprising a lubricant and between about 0.1% and about 10% by weight of the total composition of the reaction product resulting from the process of claim 3.

* * * * *